(12) United States Patent
Nelson et al.

(10) Patent No.: US 11,566,036 B2
(45) Date of Patent: Jan. 31, 2023

(54) METHODS FOR PREPARING METAL CARBOXYLATES IN ONE-POT REACTION

(71) Applicant: KEMIN INDUSTRIES, INC., Des Moines, IA (US)

(72) Inventors: Christopher E. Nelson, Cumming, IA (US); Umesh Balakrishnan, Chennai (IN); Buddhi Sreeramulu Nandhakumar, Chennai (IN); Kottakulam Mani Murugan, Chennai (IN); Haridasan Chirakkal, Chennai (IN)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 16/833,476

(22) Filed: Mar. 27, 2020

(65) Prior Publication Data
US 2020/0308210 A1  Oct. 1, 2020

Related U.S. Application Data

(60) Provisional application No. 62/824,784, filed on Mar. 27, 2019.

(51) Int. Cl.
| | | |
|---|---|---|
| C07F 15/06 | (2006.01) | |
| C07F 13/00 | (2006.01) | |
| C07F 3/06 | (2006.01) | |
| C07F 1/08 | (2006.01) | |

(52) U.S. Cl.
CPC ........... *C07F 15/06* (2013.01); *C07F 1/08* (2013.01); *C07F 3/06* (2013.01); *C07F 13/00* (2013.01)

(58) Field of Classification Search
CPC ... C08G 65/007; C08G 65/336; C07F 7/1804; C07F 15/06; C07F 1/08; C07F 3/06; C07F 13/00; C09D 171/00
See application file for complete search history.

(56) References Cited

U.S. PATENT DOCUMENTS

| | | | | | |
|---|---|---|---|---|---|
| 3,008,986 | A | * | 11/1961 | Archibald | C07C 51/412 562/606 |
| 4,592,915 | A | * | 6/1986 | Goyette | A23K 30/15 426/321 |
| 4,700,000 | A | * | 10/1987 | Merkel | C07C 51/412 562/606 |
| 5,591,878 | A | * | 1/1997 | Nelson | C07C 51/412 556/49 |
| 5,689,000 | A | * | 11/1997 | Ebner | B01J 37/0217 562/539 |
| 5,707,679 | A | * | 1/1998 | Nelson | C07C 51/412 426/635 |
| 5,795,615 | A | * | 8/1998 | Nelson | C07C 51/412 426/648 |
| 5,846,581 | A | * | 12/1998 | Catron | C07C 51/412 426/74 |
| 5,965,414 | A | * | 10/1999 | Vandenbergh | A23C 19/062 435/170 |
| 8,293,793 | B2 | * | 10/2012 | Hauk | A23K 20/22 514/578 |
| 8,575,212 | B2 | * | 11/2013 | Knochenmus | C07F 15/065 423/151 |
| 9,663,438 | B2 | * | 5/2017 | Reddy | C07C 51/412 |
| 10,265,340 | B2 | * | 4/2019 | LeBrun | A23K 50/10 |
| 2002/0120402 | A1 | * | 8/2002 | Burghardi | A23K 50/80 702/19 |
| 2003/0185877 | A1 | * | 10/2003 | Betz | A61K 8/67 241/21 |
| 2007/0269495 | A1 | * | 11/2007 | Ashmead | A61K 31/28 514/184 |
| 2008/0317934 | A1 | * | 12/2008 | Hauk | A23K 50/75 426/635 |
| 2012/0223634 | A1 | * | 9/2012 | Xia | H01L 51/0087 313/504 |
| 2012/0228583 | A1 | * | 9/2012 | Wu | C07F 15/0033 257/40 |
| 2013/0129818 | A1 | * | 5/2013 | Bernick | A61K 9/4825 424/451 |
| 2013/0216586 | A1 | * | 8/2013 | LeBrun | A61K 31/716 424/278.1 |
| 2014/0084261 | A1 | * | 3/2014 | Brooks | H01L 51/0072 257/40 |
| 2014/0138653 | A1 | * | 5/2014 | Tsai | H01L 51/0088 257/40 |

(Continued)

FOREIGN PATENT DOCUMENTS

| | | |
|---|---|---|
| EP | 0902787 B1 | 5/2002 |
| WO | 96/10553 A1 | 4/1996 |
| WO | 1998033398 A1 | 8/1998 |

OTHER PUBLICATIONS

J. Chaumeil et al., 20 Methods and Findings in Experimental and Clinical Pharmacology, 211-215 (1998) (Year: 1998).*
G. Predieri et al., 362 Inorganica Chimica Acta, 1115-1121 (2009) (Year: 2009).*
International Searching Authority, "Search Report and Written Opinion," issued in connection with International Patent Application No. PCT/US2020/025550, dated Jun. 19, 2020, 10 pages.
International Searching Authority, "International Preliminary Report on Patentability," issued in connection with International Patent Application No. PCT/US2020/025550, dated Oct. 7, 2021, 9 pages.

(Continued)

*Primary Examiner* — Alexander R Pagano
(74) *Attorney, Agent, or Firm* — Nyemaster Goode P.C.

(57) ABSTRACT

The present invention relates to methods of manufacturing multiple metal propionates in a single reaction using sodium hydroxide as initiator and propionic acid as solvent. The method provides up to 95% conversion with greater than 60% yield. In addition, the method significantly reduces the cost or production by shortening reaction time, eliminating secondary mixing process, and providing simultaneous drying and micronization steps.

11 Claims, 2 Drawing Sheets

(56) References Cited

U.S. PATENT DOCUMENTS

| | | | | |
|---|---|---|---|---|
| 2015/0028290 A1* | 1/2015 | Xia | .................... | H01L 51/0067 |
| | | | | 257/40 |
| 2015/0194612 A1* | 7/2015 | Tsai | ....................... | C09K 11/06 |
| | | | | 257/40 |
| 2016/0289180 A1 | 10/2016 | Leonardi et al. | | |
| 2017/0066707 A1* | 3/2017 | Reddy | ................... | C07C 53/122 |
| 2017/0136035 A1* | 5/2017 | Cafiero | .................. | A61K 31/40 |
| 2018/0206528 A1* | 7/2018 | Costigan | ................ | A23K 20/00 |
| 2018/0370999 A1* | 12/2018 | Tsai | .................... | H01L 51/0072 |
| 2019/0002346 A1* | 1/2019 | Wings | .................. | C04B 14/106 |
| 2019/0214583 A1* | 7/2019 | Ji | ....................... | H01L 51/0054 |
| 2019/0262381 A1* | 8/2019 | LeBrun | ................. | A23K 50/10 |
| 2019/0328004 A1* | 10/2019 | Johnson | ................ | A23K 10/30 |

OTHER PUBLICATIONS

Sivasankar et al., "Stuides on Bis-hydrazine Complexes of Metal Propionates and Mixed Metal Propionates," Verlag der Zeitschrift fur Naturforschung, Jan. 12, 1994, 5 pages.

Bassi et al., "Comparative Sudy of the Thermal Analyses of Some Transition Metal(II) Propionates, Part 1," Thermochimica Acta, vol. 71, 1893, pp. 15-24.

Lis, T., "Manganese(II) Propionate Dihydrate," Acta. Cryst., vol. B33, 1977, pp. 2964-2966.

\* cited by examiner

Figure 1:
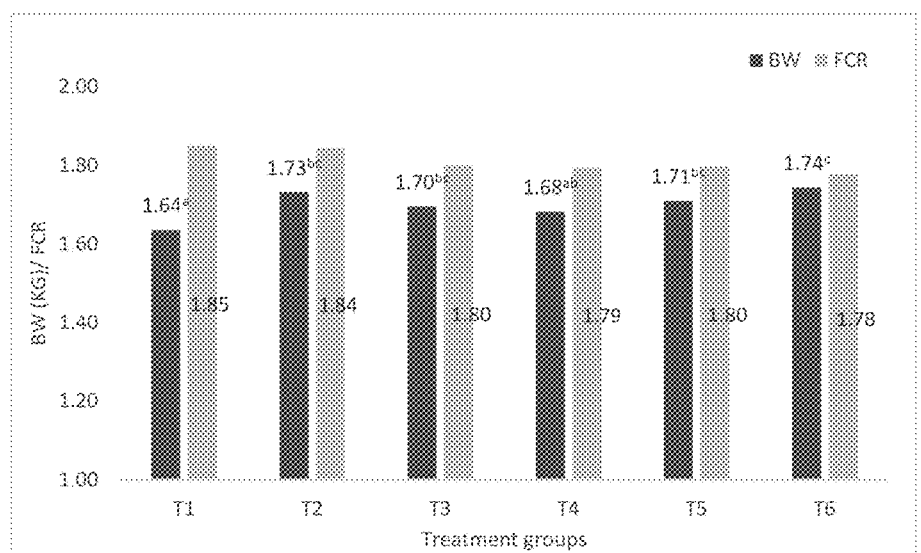

FIG. 1. T1= Inorganic minerals @ 1000g/ton of feed, T2= Proteinate mineral @ 250 g/ton of feed, T3= OPS blend with inorganic minerals @ 250 g/ton of feed, T4= Individual metal propionate with inorganic minerals @ 350 g/ton of feed, T5= OPS with complete organic minerals @ 500 g/ ton of feed, T6= OPS with complete organic minerals @ 500g/ton of feed.

Figure 2:
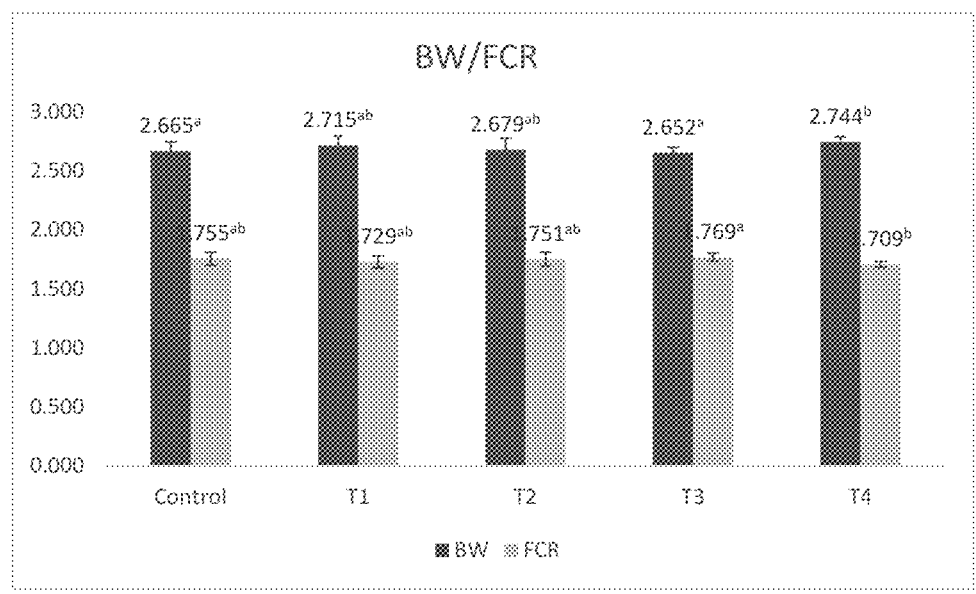

FIG. 2. C= Positive Ctrl, T1= Competitor proteinate minerals -1 @350g, T2= Competitor proteinate minerals-2 @500g, T3= Competitor -3 proteinate minerals @500g, T4= OPS @ 500g per ton of feed.

METHODS FOR PREPARING METAL CARBOXYLATES IN ONE-POT REACTION

CROSS-REFERENCE TO RELATED APPLICATIONS

This application claims the benefit of priority to U.S. Provisional Patent Application No. 62/824,784, filed Mar. 27, 2019, entitled "METHODS FOR PREPARING METAL CARBOXYLATES," the disclosure of which is hereby incorporated herein by reference in its entirety.

BACKGROUND OF THE INVENTION

Trace minerals are essential components of animal feed for normal function, reproduction, immunity and production. A mineral must become soluble before it can readily dissociate. As such, minerals with low solubilities, such as metal oxides and carbonates, have a relatively less chance for eventual cellular uptake. Alternatively, if too much of a mineral dissociates in the rumen or dissociates before reaching the intestinal binding sites, the mineral may be recompiled to form tightly bound complexes with anti-nutritional elements present in the feed that may simply wash through the system without the mineral being utilized. In addition, some minerals, even after absorption, may not be utilized by the animal and may excrete through the urine or feces.

Metal propionate minerals are highly soluble, dissociate at a rate that is approximately equal to the need or availability of the respective metal transport sites through the gastrointestinal tract. Further, metal propionate minerals are highly absorbed and maximally retained.

Current processes of manufacturing metal propionates produce individual minerals, and mainly include acid-base catalyzed reaction at 110±5° C. for six to twelve hours using carbonates and oxide as metal source, propionic acid as ligand and sodium hydroxide as initiator, as set forth below:

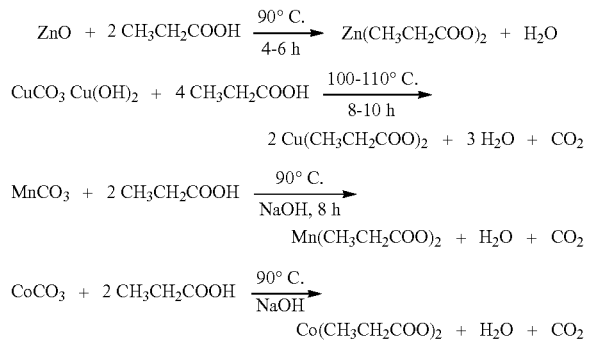

The rate of formation of product is different for each metal propionate. The production cost of metal propionates using these methods, including energy cost, labor cost, cost of switchover between batches and secondary blending process, accounts for approximately 30% of the cost of the final formulated products. There is therefore a continued need to develop a cost-effective process of preparing metal propionates.

SUMMARY OF THE INVENTION

The present invention relates to methods of manufacturing metal propionates in a single reaction using sodium hydroxide as an initiator, or alternatively known alkali hydroxides such as potassium hydroxide, and propionic acid as a solvent, or alternatively any C2 to C4 carboxylic acid. The general reaction can be depicted as follows:

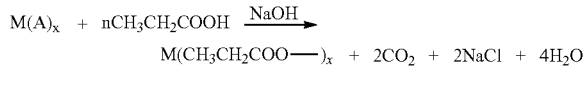

wherein M is a polyvalent metal cation form of said deficient metal;

A is an anion of a metal salt such as carbonates, oxides, sulfates and chlorides or molecule that binds to the metal atom to form a coordination complex; and x is an integer equal to the cationic charge of M.

The present invention, referred to as a "one-pot synthesis" method, relates to methods of manufacturing multiple metal propionates (OPS) in a single reaction using sodium hydroxide as initiator and propionic acid as solvent. The method provides up to 95% conversion with greater than 65% yield. In alternative embodiments, multiple metal propionates are produced with greater than 65% conversion and greater than 60% yield. Other aspects of the present invention relate to methods to significantly reduce the cost or production by shortening reaction time, eliminating secondary mixing process, improving yields, and providing simultaneous drying and micronization steps.

DETAILED DESCRIPTION OF THE FIGURES

FIG. 1 is a graph illustrating the performance of the experimental groups on day 35 as described in Example 1: (n=8, mean±SD), T1=Inorganic minerals @ 1000 g/ton of feed, T2=Proteinate mineral @ 250 g/ton of feed, T3=OPS blend with inorganic minerals @ 250 g/ton of feed, T4=Individual metal propionate with inorganic minerals @ 350 g/ton of feed, T5=OPS in complete organic formulation @ 250 g/ton of feed, and T6=OPS in complete organic @ 500 g/ton of feed. BW=body weight, FCR=feed conversion ratio. The effect of organic minerals on body weight gain (BWG) for chickens at 0-35 days. A. BWG 0-28 days. B. BWG 29-47 days.

FIG. 2 is a graph illustrating that reformulation of KemTRACE products with one pot mineral product (KemTRACE premium) improved body weight and FCR (feed conversion ratio) of broilers against major competitor products. As shown, the performance of the experimental groups on day 42, (n=8, mean±SD), C-KemTRACE Broiler (individual metal propionate) @ 500 g/ton, T1=Competitor-1 (proteinate mineral) @ 350 g/ton, T2=Competitor-2 (proteinate mineral) @ 500 g/ton, T3=Competitor-3 (proteinate mineral) @ 500 g/ton, and T4=OPS KemTRACE (OPS minerals) @ 500 g/ton of feed.

DETAILED DESCRIPTION OF THE INVENTION

The present invention describes the simultaneous production, for instance a one-pot synthesis, of different metal carboxylates in dry micronized form using a turbo reactor. The present invention has many advantages, including synthesis in less time than known, conventional processes. The method provides the advantages of high conversion rates and yields, while lowering the cost of production and shortening reaction times. In addition, different metal carboxylates can be simultaneously synthesized, in contrast to previous methods which require the synthesis of each metal carboxylate separately.

One aspect of the present invention relates to placing one or more sources (i.e. salts) of different polyvalent metal cations in a reactor along with propionic acid and sodium hydroxide, or alternatively an alkali hydroxide catalyst. According to at least one embodiment, the reactor is a turbo dry reactor under vacuum. In at least one embodiment, the metal sources are sulfate, chloride, carbonate or hydroxide, or oxide salts. The concentration ratio of metal:ligand:catalyst may vary based on composition of metal source but should be minimum of 1:2.2:1. Step-by-step addition helps to produce the desired product over undesired parallel reactions, which means that caustic should react only with manganese or cobalt salts and not with zinc or copper salts. According to at least one embodiment, manganese and cobalt are added first, followed by caustic and then other raw materials. This stepwise addition reduces undesirable byproducts and improves the overall yield. The present invention is further unique in that it allows for synthesis of metal carboxylates using a metal sulfate source which, to date, had not yet been achieved.

The mixture should be heated to a temperature capable of distilling the solvent. According to at least one embodiment, the mixture is heated to a temperature of at least 92±5° C. to provide complete conversion, and preferably at temperatures in the range of 100-110° C. The ingredients can be mixed with varying degrees of agitation. The overall reaction using zinc, manganese, cobalt and copper salts can be depicted as follows:

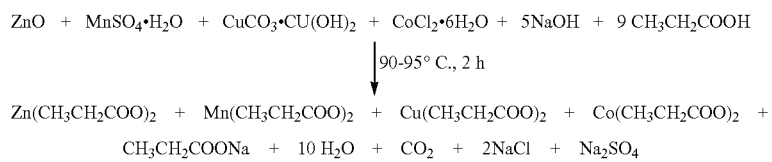

The total reaction yield is typically about 70±5% with total processing time of about 2-4 hours. The reaction should be allowed to continue for a time of at least 30 minutes to obtain a high degree of conversion. According to alternative embodiments, the reaction should be allowed to continue for about 30 to 100 minutes, such as about 70 minutes, about 80 minutes or about 90 minutes. In at least one embodiment, the reaction, drying and micronation all takes place in a single system or turbo reactor.

Once the reaction is complete, the resulting product is very sticky due to the tacky nature of propionic acid and by-product. The reaction mixture is next dried under vacuum to remove liquid as condensate in the range of about 75 to 90% of total condensate that to be collected. The range of liquid to be removed depends on metals composition. After removal of desired quantity of liquid as condensate, the heating and cooling process to be repeated at least once to remove remaining quantity of liquid under atmospheric pressure As already noted, the general reaction to produce the metal propionates of the invention can be depicted as follows:

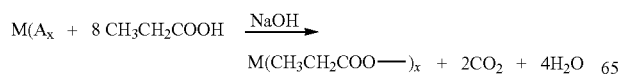

wherein M is a polyvalent metal cation form of said deficient metal;

A is an anion of a metal salt such as carbonates, oxides, sulfates and chlorides or molecule that binds to the metal atom to form a coordination complex; and x is an integer equal to the cationic charge of M.

In the formula, M is preferably a divalent or trivalent metal. In one embodiment, M is a metal selected from the group consisting of $Zn^{+2}$, $Cu^{+2}$, $Fe^{+3}$, $Fe^{+2}$, $Mn^{+2}$, $Co^{+2}$, and $Cr^{+3}$. In one embodiment, A is a halogen or chalcogen. In another embodiment, A is chloride, oxide, hydroxide or sulfate and carbonate.

The invention produces different metal carboxylates in a single reaction, optionally using a turbo reactor under vacuum condition by a unique process to achieve reaction, drying, and micronization in a single system. By producing multiple metal carboxylates in a single reaction, the following is achieved: 1) reduced cycle time; 2) reduced effluent discharge; 3) optimization of labor and/or operation costs; 4) production capacity from 1-4 tons per shift; and 5) simultaneous reaction, drying, and micronization.

The metal carboxylates synthesized in accordance with the invention are typically used in animal feed, and can be formulated to include other ingredients or compounds that may be beneficial for poultry or other animals including, but not limited to, carbohydrate, protein, fat and oil, vitamins, minerals, probiotics, medicines, flavors, colors, etc. The compositions may also be combined with a pharmaceutically acceptable carrier that may include one or more carriers or excipients, such as fillers, diluents, binders, lubricants, and disintegrants. Such ingredients and their relative amounts to be included are well known to persons skilled in the art.

While the compositions of the invention are described in particular for administration in the animal's feed, the compositions may likewise be administered in the animal's water source. In addition, the compositions may be administered via conventional pharmaceutical routes including, but not limited to, intravenously, rectally, sublingually, etc. via a pharmaceutical carrier appropriate to the selected route of administration.

The following examples are offered to illustrate but not limit the invention. Thus, it is presented with the understanding that various formulation modifications as well as method of delivery modifications may be made and still are within the spirit of the invention.

EXAMPLES

Methods and Materials:

Metal propionates were synthesized using the following compounds and reaction conditions in a turbo reactor:

ZnO + MnSO$_4$·H$_2$O + CuCO$_3$·CU(OH)$_2$ + CoCl$_2$·6H$_2$O + 5NaOH + 9 CH$_3$CH$_2$COOH $\downarrow$ 90-95° C., 2 h Zn(CH$_3$CH$_2$COO)$_2$ + Mn(CH$_3$CH$_2$COO)$_2$ + Cu(CH$_3$CH$_2$COO)$_2$ + Co(CH$_3$CH$_2$COO)$_2$ + CH$_3$CH$_2$COONa + 10 H$_2$O + CO$_2$ + 2NaCl + Na$_2$SO$_4$ Results:

TABLE 1

Pilot-scale batch results of multiple minerals

| Parameters | *Trial -1 | *Trial -2 | *Trial -3 | **Trial -4 | **Trial -5 | **Trial -6 |
|---|---|---|---|---|---|---|
| Total Input | 12.00 kg | 12.00 kg | 12.00 kg | 12.00 kg | 12.00 kg | 12.00 kg |
| Total output (Dry Product) | 8.17 kg | 8.23 kg | 8.28 kg | 8.43 kg | 8.23 kg | 8.10 kg |
| Total distillate (Liquid) | 3.30 kg | 3.45 kg | 3.42 kg | 3.40 kg | 3.40 kg | 3.51 kg |
| % MB Yield | 95.6 | 97.3 | 97.5 | 98.6 | 97.4 | 96.8 |
| % Propionic acid in distillate | 38.2 | 41 | 40.6 | 41.5 | 40.8 | 42.5 |
| Moisture content (%) | 1.1 | 0.56 | 1.4 | 0.5 | 0.86 | 1.2 |
| Solubility in water | >5% | >5% | >5% | >5% | >5% | >5% |
| Color | Greenish blue | Greenish blue | Greenish blue | Greenish blue | Greenish blue | Greenish blue |
| Nature of material formed | Lump | Lump | Lump | Powder | Powder | Powder |
| Drying time | 98 | 100 | 130 | 90 | 89 | 95 |
| Cooling time | 45 | 58 | 50 | 33 | 35 | 35 |

*Caustic Lye was used as a Sodium hydroxide source in reaction
**Sodium hydroxide pellets were used as a Sodium hydroxide source in reaction

TABLE 2

Results from Multiple Trials

| Parameters | Trial 1 | Trial 2 | Trial 3 | Trial 4 | Trial 5 |
|---|---|---|---|---|---|
| Total Input | 138.31 g | 137.14 g | 134.06 g | 138.86 g | 133.9 |
| Total output | 134 g | 132 g | 130 g | 135.5 g | 129.5 g |
| Output (distillate alone) | 57 g | 52 g | 54 g | 60 g | 50.5 g |
| Output (dry) | 77 g | 80 g | 76 g | 75.5 g | 79 g |
| % MB Yield | 96.88 | 96.2 | 97.07 | 97.5 | 96.7 |
| % Propionic acid in distillate | 27.83 | 24.61 | 27.42 | 28.67 | 28.11 |
| LOD (Loss on drying) | 4% | 5% | 4.8% | 5.1% | 4.6% |
| pH (@1% in water) | 5.567 | 5.653 | 5.548 | 5.546 | 5.663 |
| Solubility | 10% | 10% | 10% | 10% | 10% |
| Color | Bluish green | Bluish green | Bluish green | Bluish green | Bluish green |

TABLE 3

Large-scale batch results of multiple minerals

| Parameters | Trial #1 | Trial #2 | Trial #3 | Trial #4 | Trial #5 | Trial #6 | Trial #7 | Trial #8 | Trial #9 | Trial #10 | Trial #11 |
|---|---|---|---|---|---|---|---|---|---|---|---|
| Total Input (kg) | 2004.3 | 2004.4 | 2003.4 | 2008.2 | 2004.4 | 2000.9 | 2011.6 | 2004.3 | 1948.0 | 1942.8 | 1951.9 |
| Actual dry product output (kg) | 1622.4 | 1574.0 | 1545.0 | 1675.0 | 1586.0 | 1477.0 | 1684.0 | 1568.0 | 1628.0 | 1610.0 | 1560.0 |

TABLE 3-continued

Large-scale batch results of multiple minerals

| Parameters | Trial # 1 | Trial # 2 | Trial # 3 | Trial # 4 | Trial # 5 | Trial # 6 | Trial # 7 | Trial # 8 | Trial # 9 | Trial # 10 | Trial # 11 |
|---|---|---|---|---|---|---|---|---|---|---|---|
| Yield % | 80.9% | 78.5% | 77.1% | 83.4% | 79.1% | 73.8% | 83.7% | 78.2% | 83.6% | 82.9% | 79.9% |
| Total condensate (kg) | 325.0 | 350.0 | 347.0 | N/A | 362.0 | 348.0 | 348.0 | 352.0 | 290 | 302.0 | 327.0 |
| Mass Balance % | 98.6 | 97.4 | 95.9 | 98.5 | 98.6 | 92.6 | 102.4 | 97.2 | 99.9 | 99.9 | 98.2 |
| % Propionic acid in condensate | 44.9 | 49.5 | 45.6 | N/A | 44.8 | 49.8% | 43.4% | 40.5% | 31.5 | 40.5 | 41.1 |
| Moisture content (%) | <0.46 | <0.65 | <0.7 | <2 | <2 | <2 | <2 | <2 | <2 | <2 | <2 |
| pH | 5.5-6.5 | 5.5-6.5 | 5.5-6.5 | 5.5-6.5 | 5.5-6.5 | 5.5-6.5 | 5.5-6.5 | 5.5-6.5 | 5.5-6.5 | 5.5-6.5 | 5.5-6.5 |
| Solubility in water (in 2% dilution) (%) | >98.0 | >98.0 | >98.0 | >98.0 | >98.0 | >98.0 | >98.0 | >98.0 | >98.0 | >98.0 | >98.0 |
| Color (Greenish blue) | Greenish blue | Greenish blue | Greenish blue | Greenish blue | Greenish blue | Greenish blue | Greenish blue | Greenish blue | Greenish blue | Greenish blue | Greenish blue |
| Nature of material formed | Powder | Powder | Powder | Powder | Powder | Powder | Powder | Powder | Powder | Powder | Powder |
| Total Batch time (min) | 340 | 341 | 297 | 272 | 269 | 259 | 268 | 272 | 256 | 269 | 272 |
| Total Batch time (hours) | 5.67 | 5.68 | 4.95 | 4.53 | 4.48 | 4.31 | 4.46 | 4.53 | 4.26 | 4.48 | 4.53 |

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The foregoing description has been presented for the purposes of illustration and description. It is not intended to be an exhaustive list or limit the invention to the precise forms disclosed. It is contemplated that other alternative processes and methods obvious to those skilled in the art are considered included in the invention. The description is merely examples of embodiments. It is understood that any other modifications, substitutions, and/or additions may be made, which are within the intended spirit and scope of the disclosure. From the foregoing, it can be seen that the exemplary aspects of the disclosure accomplishes at least all of the intended objectives.

The invention claimed is:

1. A method of manufacturing two or more metal propionates in a one-pot synthesis reaction comprising mixing at least one metal sulfate with at least one metal salt selected from the group consisting of metal carbonates, metal oxides, metal sulfates and metal chlorides with propionic acid in the presence of an alkali hydroxide in a single reactor to form a product comprising two or more metal propionates, whereby the metal is selected from the group consisting of zinc, manganese, cobalt, and copper.

2. The method according to claim 1, comprising drying and micronization the product and wherein the steps of mixing, drying and micronization are carried out in a single system.

3. The method of claim 1 wherein the product comprises less than about 0.2% by weight moisture with a particle size of less than about 500 microns.

4. The method of claim 1 wherein the reaction occurs at a temperature of at least 70° C.

5. The method of claim 4 wherein the temperature is 92±5° C.

6. The method of claim 1 wherein the batch time is about two to four hours.

7. The method of claim 1 further including the step of agitating the product.

8. The method of claim 1 wherein the product yield is at least 65% by weight.

9. The method of claim 8 wherein the product yield falls within the range of about 65 to about 95% by weight.

10. The method of claim 1 having a yield of greater than 60% by weight.

11. The method of claim 10 having a yield of greater than 75% by weight.

* * * * *